Dec. 9, 1969 H. C. SWIM ET AL Plant Pat. 2,945
ROSE PLANT
Filed Oct. 18, 1967
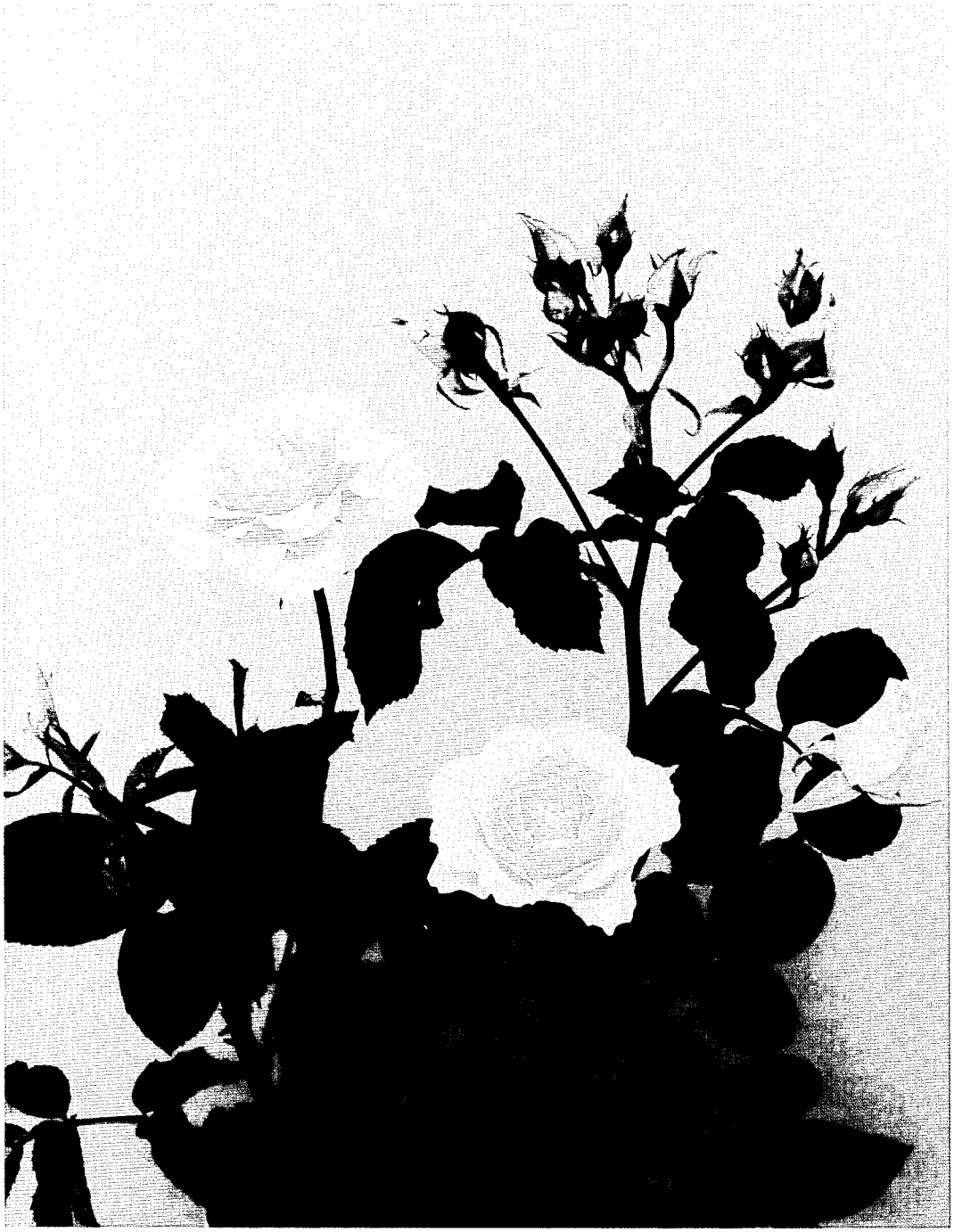

United States Patent Office

Plant Pat. 2,945
Patented Dec. 9, 1969

2,945
ROSE PLANT

Herbert C. Swim, Ontario, Calif., and O. L. Weeks, 926 Philadelphia, Ontario, Calif. 91762; said Swim assignor to said O. L. Weeks, doing business as Weeks Wholesale Rose Grower, Chino, Calif.

Filed Oct. 18, 1967, Ser. No. 676,365
Int. Cl. A01h 5/02
U.S. Cl. Plt.—22 1 Claim The present invention relates to a new and distinct variety of rose plant of the floribunda class. The plant is a bush type, of seedling origin, and particularly adapted to greenhouse culture and the production of cut flowers.

The variety was originated by us by crossing Verona (Plant Patent No. 2,282) with Escort (Plant Patent No. 2,436). As a result of this breeding we have selected, and have asexually reproduced a new and improved rose variety having characteristics which are outstanding therein, and which, together, distinguish it from its parents as well as all other varieties of which we are aware.

The shape of the bud, the contours of the petals in the open flower, the arrangement of those petals and their evident crispness and substance, and the gradations of pink shades in the flower are quite distinctive. The capacity of the plant to maintain substantially continuous production of relatively uniform quality flowers under greenhouse conditions is unusual.

We believe that the lasting quality of its flowers is outstanding, when cut from plants grown under greenhouse conditions. We know of only one rose of the floribunda class which is capable of producing flowers of comparable longevity, namely the variety known as Rosenelfe, the flowers of which, although quite different in shape, would also be referred to as pink roses. However, an important advantage in the present variety, from the standpoint of commercial growers, is that it is relatively insensitive to daytime temperature changes such as result when a few days of unusually warm, clear weather are followed by a spell of cool, cloudy weather. Such changes seem to have little effect on the production or form of buds and flowers in this new variety, whereas, with Rosenelfe, similar changes may result in foreshortening of the buds, and the production of malformed blooms. The characteristic resistance to environmental change which pertains to our new variety of rose not only leads to the production of cut flowers of more uniform quality; it also reduces the degree of care which is needed to counteract such changes during the growing phase.

Another variety of rose plant which is related to the present variety is Pink Flair, which, however, does not have the longevity or other characteristics of the new variety. Furthermore, the peduncles on Pink Flair are not as consistently straight as those of the present variety, and the coloration on the outer surfaces of the bud is substantially deeper than in this new variety.

In comparison with its seed parent Verona, the flowers of the present variety are of a medium pink shade, whereas the flowers of Verona are light pink. The new variety has greater petal substance and stiffness than does Verona, and it manifests substantially longer vase life, as a cut flower, in part because of this characteristic. The outer petals of this new variety have a pronounced incurvature along the lateral margins, whereas the outer panels of Verona are relatively flat, or even reflexed, along the lateral margins.

This new variety is distinct from its pollen parent, Escort, in the following ways. The flowers of Escort would be described as dark red, as compared to the medium pink shade of the present variety. The flowers of this new variety have substantially longer vase life and greater petal substance than does Escort. The flowers of the new variety have substantially more petals than the flowers of the Escort rose. The peduncles of this new variety are substantially shorter than those of Escort.

The rose known as Pink Flair has been referred to above, this being a variety produced from the same breeding. However, the new variety is substantially more erect in its natural growth habit than is Pink Flair, and, as noted, the peduncles of this new variety are relatively straight, which is in marked contrast to the tendency of Pink Flair to develop excessively long and twisted peduncles, particularly under dark winter conditions. Furthermore, the vase life of the present variety, as a cut flower, is, on the average, about twenty percent longer than that of the flowers of Pink Flair, under comparable conditions.

The new variety was first asexually reproduced by budding in Ontario, Calif., in the month of September. The specimens described herein were grown in a greenhouse in Los Angeles, Calif.

The plant holds its distinguishing characteristics continuously through succeeding propagations, under greenhouse conditions. The blooms are moderately fragrant, having an aroma reminiscent of the tea roses. The flowers may be borne singly, or sometimes two or three together, on normal stems of medium to long length. Sometimes several flowers may be carried by one strong stem, usually of medium to long length, in which case they tend to form a regularly arranged but more or less flat cluster. The quantity of bloom ranges from free to abundant, under greenhouse cultivation.

The accompanying drawing portrays the new plant variety in color, and illustrates the development of the flower from bud to full blown maturity. It also shows single normal stems bearing single blooms, and one strong stem carrying a cluster of buds.

BUD

The peduncle is short to medium in length, of medium caliper, erect, and yellowish-green in color. It is slightly rough, because of a moderate quantity of stipitate glands on the surface.

Before the calyx breaks, the bud is of small to medium size, long and pointed in form, with a conspicuous neck. There are some foliaceous appendages on the surface of the bud, which usually do not extend beyond the tip of the bud. Occasionally, a sepal having a foliaceous appendage beyond the tip of the bud will be found, however.

As the calyx breaks, the color varies from a nondescript yellowish-green through Moderate Yellowish Pink 7.5R8/6, to Deep Yellowish Pink 5R6/11. The two color values last mentioned are based on the Nickerson Color Fan, which is used for identifying color and shade throughout this descripton except where more colloquial terms are sufficiently specific.

As the petals first open, the buds range from long and pointed to urn-shaped in form, and are of medium to large size for this class. The color on the outside of the outside petals varies somewhat as between the center flowers of a large cluster, carried by one of the stronger stems, and the other flowers, on more normal stems. In the central flowers, there is an area of Light Yellow Green 7.5GY9/4 at the base of the petal which follows the midrib for half or slightly more than half its length. The remainder of the petal ranges from Pale Pink 2.5R9/3 to Light Purplish Pink 7.5RP8/5, with occasional markings of Strong Purplish Pink 7.5RP7/10. On the more normal stems, the color on the outside of the outside petals is almost uniformly a Strong Purplish Pink 7.5RP7/10, except for a small area at the base, which is near Brilliant Yellow Green 2.5GY9/8.

The inside color of the outside petal, in the centrally located flowers with the strongest stems, is occasionally marred by an irregular vegetative streak, about ¼" wide or slightly wider, in an area extending along the midrib over about half, or slightly more, of the petal's length. The remainder of the inside petal surface is between Light Purplish Pink 7.5RP8/5 and Strong Purplish Pink 7.5RP7/10. In the flowers carried by the more normal stems, this surface is primarily between Strong Purplish Pink 7.5RP7/10 and Light Purplish Pink 7.5RP8/5, except for a small area at the base which is of a very light yellow green and so small as to be relatively inconspicuous. The bud opens up well.

BLOOM

The size when fully open is medium to large, for this class, being from about 3" to 3¼". The petalage is double, but the stamens are not hidden. There are from 40 to 45 petals, usually regularly arranged. There are also from 3 to 5 petaloids. The bloom is of high centered form at first, and remains high centered for most of the flower life. However, it becomes cupped to flat eventually. The petals at first hold an incurved shape along their lateral margins, and this tends to make the flower unusually slow in opening. This shape gradually changes to nearly flat, with the inner petals, some of which become very slightly recurved at the apex. At maturity, however, the dominant appearance is of a slight incurvature along the lateral margins, which gives the flower a crisp appearance.

The petals are thick and leathery, their texture being satiny both inside and outside. Veins are prominient on the outer surfaces of the petals, but not so on their inner surfaces. The shape of the outside petals is broadly obovate to nearly round. They are faintly scalloped, with apex more or less flat. The inside petals are obovate in form, often irregularly scalloped, with an apex which is either flat or just barely acute.

The following description was made from a rose grown in a greenhouse in Los Angeles, and describes a flower newly opened in the month of June.

In the flowers borne in clusters on strong stems, usually two of the outer petals have vegetatively induced color irregularities on their outer surface. These irregularities originate at the base and extend for half or more of the distance towards the apex, and are usually more or less pronounced in the area of the midrib. They sometimes deviate from this pattern on the opposite (inner) side of the outer petals. Otherwise, the remainder of the outer petal surface ranges from Light Purplish Pink 5RP8/5, which is found on flowers produced on the strongest canes, to a color which is dominated by Strong Purplish Pink 5RP7/9 on flowers produced on the more normal canes. On the latter, there is an inconspicuous yellow-green spot at the base.

The inside surface of the outer petals, like the outer surfaces of them, is variable, but normally ranges from near white to Light Purplish Pink 7.5RP8/5 in flowers carried on the strongest canes with a small area of faint yellow-green at the base, whereas in the flowers borne on the more normal canes the color approaches Strong Purplish Pink 7.5RP7/10. There is a faint yellow-green spot at the base which is usually only about ¼" in diameter.

The intermediate petals show a similar yellow-green tinge at the base, but so light as to be almost white, on their outer surfaces. The remainder of their outer surfaces ranges from near Deep Purplish Pink 7.5RP6/12 to Strong Purplish Pink 7.5RP7/10. The inside surfaces of the intermediate petals manifest the same small area at the base which is near white, but with a faintly greenish tinge. The remainder of the inner surfaces ranges from near Strong Purplish Pink 7.5RP7/10 to near Light Purplish Pink 7.5RP8/5.

With respect to the inner petals, the outer surfaces, as with the intermediate petals, manifest a very small spot which is white tinged faintly yellow-green. The remainder of the surface ranges from near Deep Purplish Pink 7.5RP6/12 to near Strong Purplish Pink 7.5RP7/10. The inside surface of the inner petals, except for the white-green spot at the base, is rather uniformly Strong Purplish Pink 5RP7/9.

The foregoing description of a newly opened flower was found to be equally applicable to a bloom which had been open for three days indoors, during the month of June, in Chino, Calif. The inner and outer surfaces of the outside petals manifested the same coloration as that of the newly opened flower and the same was true of the inner and outer surfaces of the inside petals.

The general color effect, with the newly opened flower, ranges from Light Purplish Pink 7.5RP8/5 at the outer portions of the bloom, to near Deep Purplish Pink 7.5RP6/12 in the central portion. There is no appreciable difference in coloration as between the newly opened flower and one which has been open for three days. The petals persist, and the longevity of the flower as a cut rose grown under greenhouse conditions and kept at living room temperatures was eight full days in the month of June.

REPRODUCTIVE ORGANS

The stamens are numerous, and are arranged fairly regularly about the pistils, which latter are of medium quantity.

The filaments are of medium length, white at the base and pink at the apex. Most of them carry anthers.

The anthers are small and yellow. They open almost simultaneously, and carry moderately abundant pollen, which is gold in color.

The styles are uneven, of medium length and medium caliper, and are characteristically bunched.

The stigma is translucent.

The ovaries are generally enclosed in the calyx, although some protrude therefrom.

The hips are short, ranging in form from more or less flat to almost globular.

The sepals are straight, moderately long and spear-shaped. They do not drop off.

The seeds are variable in quantity and small in size.

PLANT

Foliage

The leaves are compound, usually comprising from three to five leaflets, but occasionally as many as seven. They are present in normal quantity, are moderately large and moderately heavy and leathery. The leaflets are ovoid, with apex acute. The base ranges from round to slightly truncate and the margins of the leaflets are simply serrate. The color of the mature leaf is dark green on its upper surface and grey-green below. The young leaves have an upper surface which is very dark purplish red, except for a midrib which is dark green. The under surfaces of the young leaves are generally of normal green, but carry a heavy overlay of purplish red, which is less intense in the area of the midrib.

The supporting stem of the compound leaf, or rachis, is of medium weight and caliper. Its upper side is grooved, the ridges being sparsely lined with stipitate glands and short hairs. The under side is often smooth, but sometimes carries one or two prickles. The stipules are short and narrow with short points turning out at an angle of about 90°.

Roses of the new variety, when grown in a greenhouse with other well known greenhouse varieties, and under comparable conditions, show about the same degree of resistance to Powdery Mildew as do the other varieties of its class and general flower color.

Growth

The plant is of upright habit, much branched, and is characterized by vigorous growth and canes of medium caliper. The main stems are a light dull yellow green, and carry several medium length straight large prickles, with bases of short to medium length and breadth. These prickles are a grey-brown color. The stems also carry a few grey-brown small prickles, but no hairs.

The branches are bright yellow green, and carry several large straight prickles of medium length, with medium long and medium width bases. These large prickles are brown in color. The small prickles are few in number and are also brown in color. There are no hairs.

New shoots are likely to carry several large prickles which are reddish purple in color, straight in form and of medium length. These prickles have bases of medium length and medium breadth. The small prickles on the new shoots are few in number, but are also reddish purple in color. There are no hairs.

We claim:

1. The new variety of rose plant of the floribunda class, distinguished by the combination of the form of the bud, the coloration, petal crispness and petal contours of the flower, and the relative straightness of the peduncles, all substantially as herein shown and described, and having as outstanding characteristics in comparison with other roses of its class, a marked ability, under greenhouse culture, to withstand changes in temperature and light; to produce a greater proportion of good quality, blooms; and to produce blooms of substantially prolonged vase life, as cut flowers.

No references cited.

ROBERT E. BAGWILL, Primary Examiner